US00PP35090P2

(12) United States Plant Patent
Hardigan et al.

(10) Patent No.: US PP35,090 P2
(45) Date of Patent: Apr. 11, 2023

(54) RED RASPBERRY PLANT NAMED 'FINNBERRY'

(50) Latin Name: ***Rubus idaeus* L.**
Varietal Denomination: Finnberry

(71) Applicant: The United States of America, as represented by the Secretary of Agriculture, Washington, DC (US)

(72) Inventors: Michael A. Hardigan, Corvallis, OR (US); Chad E. Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/829,023

(22) Filed: May 31, 2022

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

*Primary Examiner* — Keith O. Robinson
(74) *Attorney, Agent, or Firm* — John Fado; Ariel Atkinson

(57) ABSTRACT

A new and distinct primocane-fruiting red raspberry cultivar that originated from seed produced from a cross between the primocane-fruiting red raspberry plant 'Caroline' and the red raspberry plant ORUS 4099-1, the latter of which is a sibling of the recent cultivar 'Kokanee'. This new red raspberry cultivar can be distinguished by its high yields of bright colored, medium sized berries with low defects, excellent firmness and fruit quality, and a unique flavor that is both tangy and aromatic, with a good balance to tartness and sweetness. The berries are well suited for the fresh market, and, due to their ability to be picked at early/pink stages with good flavor and continue ripening in storage with respect to color, they may offer some additional benefit for packing/shipping as a fresh market variety.

6 Drawing Sheets

Latin name of the genus and species of the plant claimed: 'FINNBERRY' is a red raspberry plant that is *Rubus idaeus* L.

Variety denomination: The new red raspberry plant claimed is of the variety denominated 'Finnberry' *Rubus idaeus* L.

BACKGROUND OF THE NEW PLANT

The present invention relates to a new and distinct red raspberry cultivar designated 'Finnberry' and botanically known as *Rubus idaeus* L. This new primocane-fruiting (fall-bearing) red raspberry cultivar was discovered in Corvallis, Oreg. in August 2014, and is the result of a 2012 cross between the maternal red raspberry plant 'Caroline' (U.S. Plant Pat. No. 10,412) and the paternal red raspberry plant ORUS 4099-1 (unpatented). 'Caroline' was a primocane-fruiting type of red raspberry derived from a cross of the female red raspberry parent 'GEO-1' (unpatented) and male red raspberry parent 'Heritage' (unpatented). ORUS 4099-1 was a selection from a cross of the primocane-fruiting red raspberry plant 'Vintage' (U.S. Plant Pat. No. 24,198) and the red raspberry ORUS 1173-2 (unpatented) and is a sibling of red raspberry cultivar 'Kokanee' (U.S. Plant Pat. No. 28,666). 'Finnberry' shows superior yields and fruit quality to both its parents, combining increased firmness, drupelet coherence, and internal texture for a high-yielding, mid-to-late season variety of red raspberry. 'Finnberry' was recognized and selected for its ability to produce fruit with low defects that can be picked early, even when still pink or light-colored, with excellent flavor and sweetness for the fresh market. The original seedling of the new cultivar was established in vitro from a root cutting and microcuttings have been taken and rooted from this sort of culture. The present invention has been found to be stable and reproduce true to type through successive asexual propagations.

SUMMARY OF THE NEW PLANT

The following are the most outstanding and distinguishing characteristics of this new cultivar when grown under normal horticultural practices in Oregon. The new cultivar possesses a primocane-fruiting habit, also known as fall bearing, with fruit ripening from mid-to-late August through Fall on first year canes. The new cultivar ripens one to two weeks later than 'Kokanee', one week later than 'Vintage', and at a similar time as 'Heritage'. The new cultivar produces canes that are more vigorous than 'Vintage', and at least as vigorous as 'Heritage', but are slightly less erect and more spreading than 'Heritage'. The new cultivar produces light-colored fruit of medium size with lower defects from UV or heat damage when compared to 'Kokanee', 'Heritage', or 'Vintage', and better firmness and coherence. The fruit can be picked at pre-ripe stages of development, even when light pink, with good flavor and still accumulate color in post-harvest storage. The new cultivar has shown fruit yields that are superior to other primocane-fruiting raspberry cultivars including 'Kokanee', 'Vintage', 'Heritage', and 'Polka' (unpatented) across multiple years and trial plantings. Thus, the cultivar appears to fit a different production window from recent primocane-fruiting cultivar standards while offering improvements in fruit yields as well as fresh market quality and potential.

BRIEF DESCRIPTION OF THE PHOTOGRAPHS

This new red raspberry plant is illustrated by the accompanying photographs that show the plants, ripening fruit morphology, and harvested fruit; the colors shown are as true as can be reasonably obtained by conventional photographic procedures.

DETAILED DESCRIPTION OF THE NEW CULTIVAR

Figure 1:
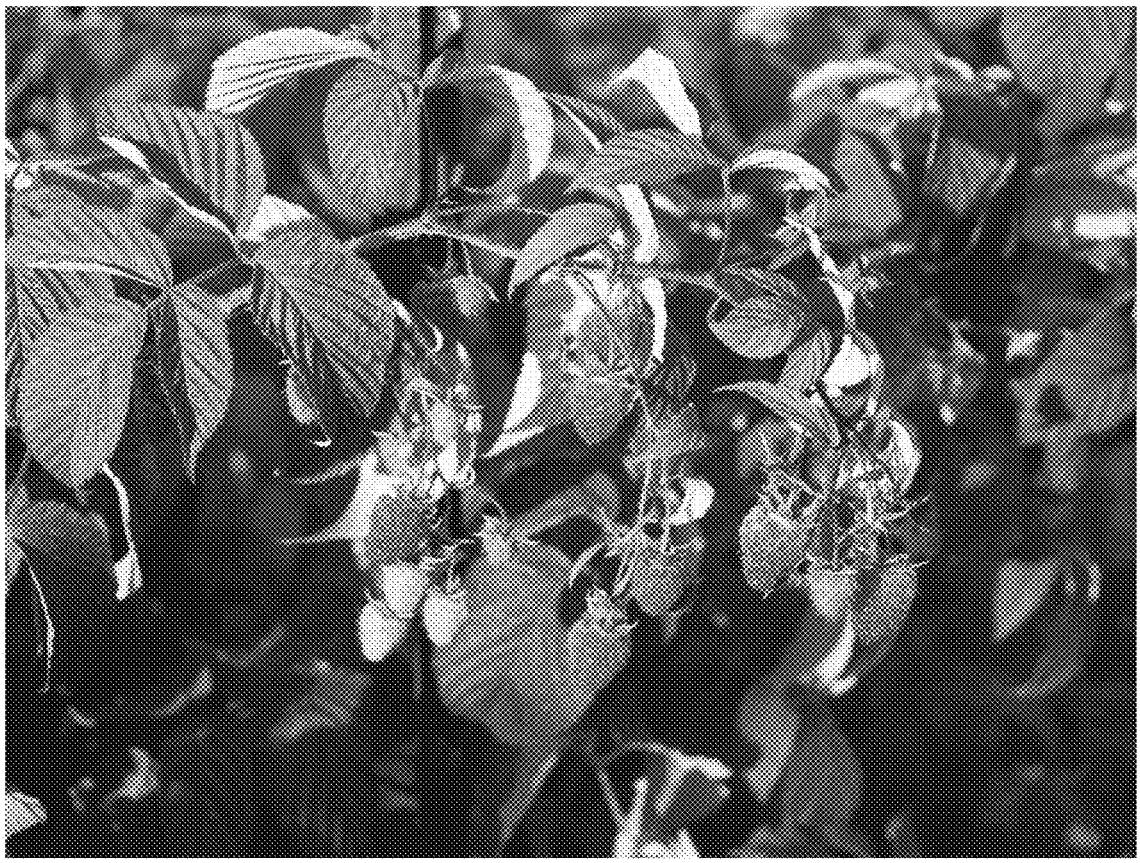
FIG. 1 shows an example of a fruiting cluster with ripe 'Finnberry' fruit.
Figure 2:
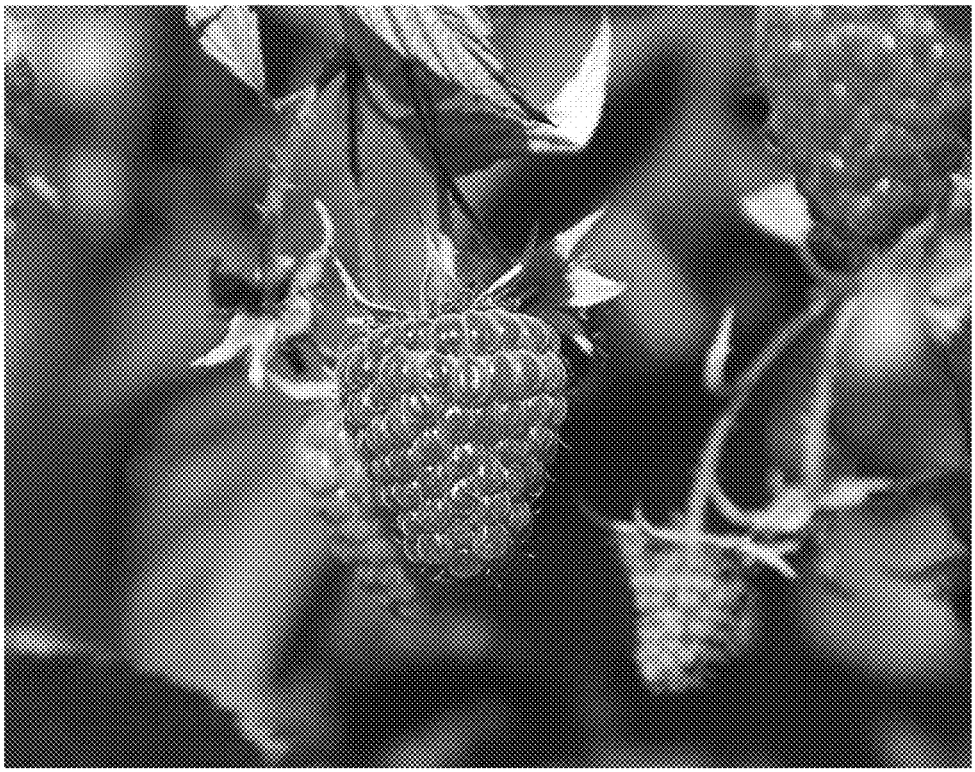
FIG. 2 shows a close-up example of the morphology of 'Finnberry' fruit and how it appears on the plant during ripening.
Figure 3:
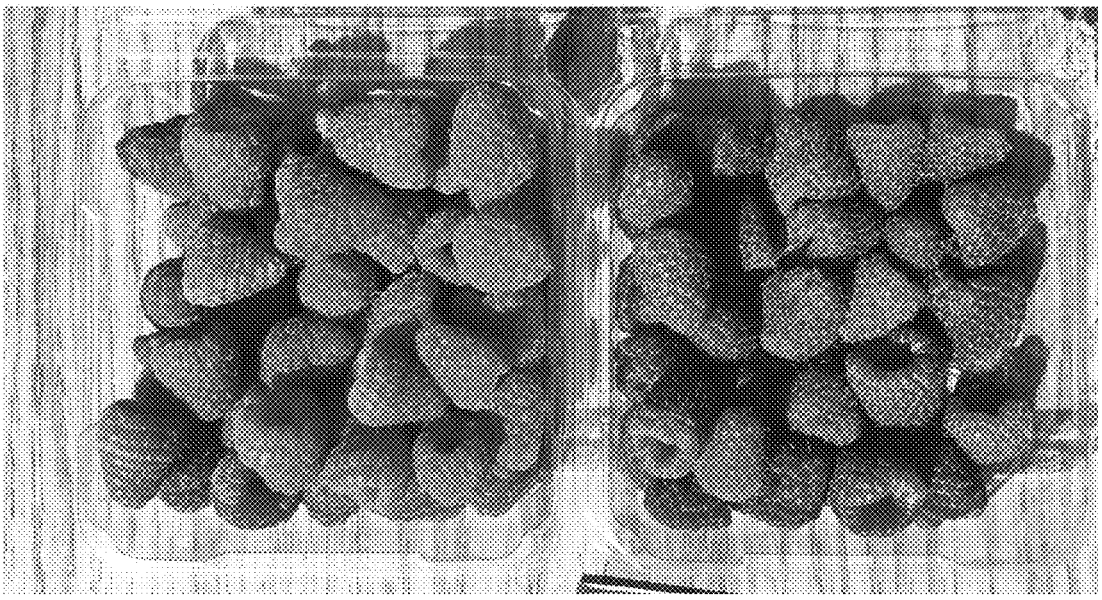
FIG. 3 shows a clamshell of 'Finnberry' fruit (left) compared to a clamshell of 'Polka' fruit (right) after 14 days of refrigerated storage at ~4° C.
Figure 4:
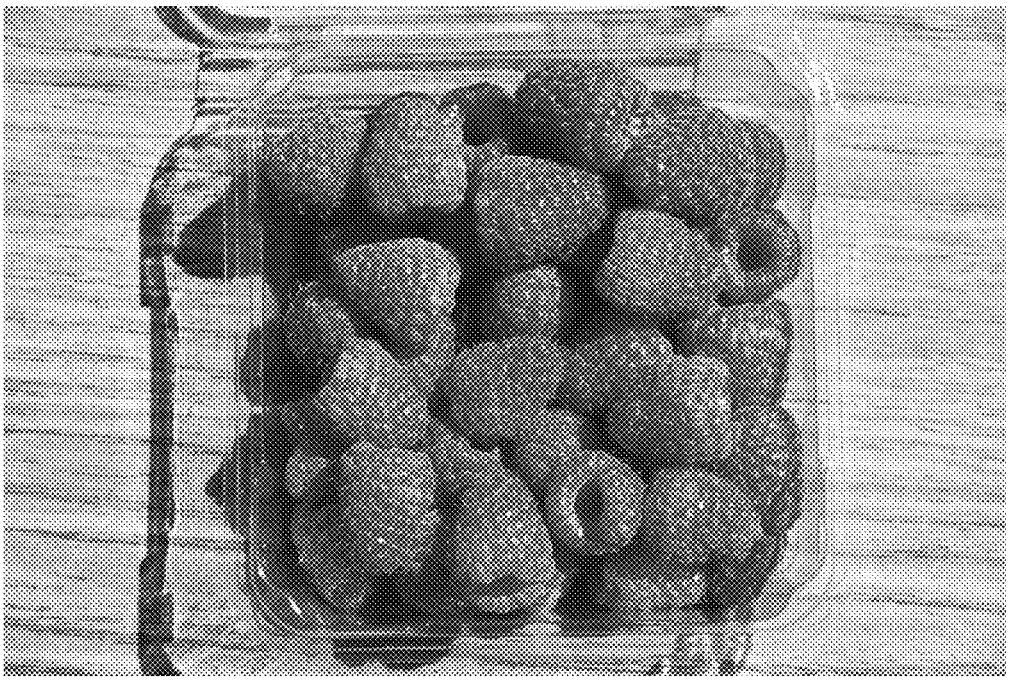
FIG. 4 shows a clamshell of freshly harvested 'Finnberry' fruit.
Figure 5:
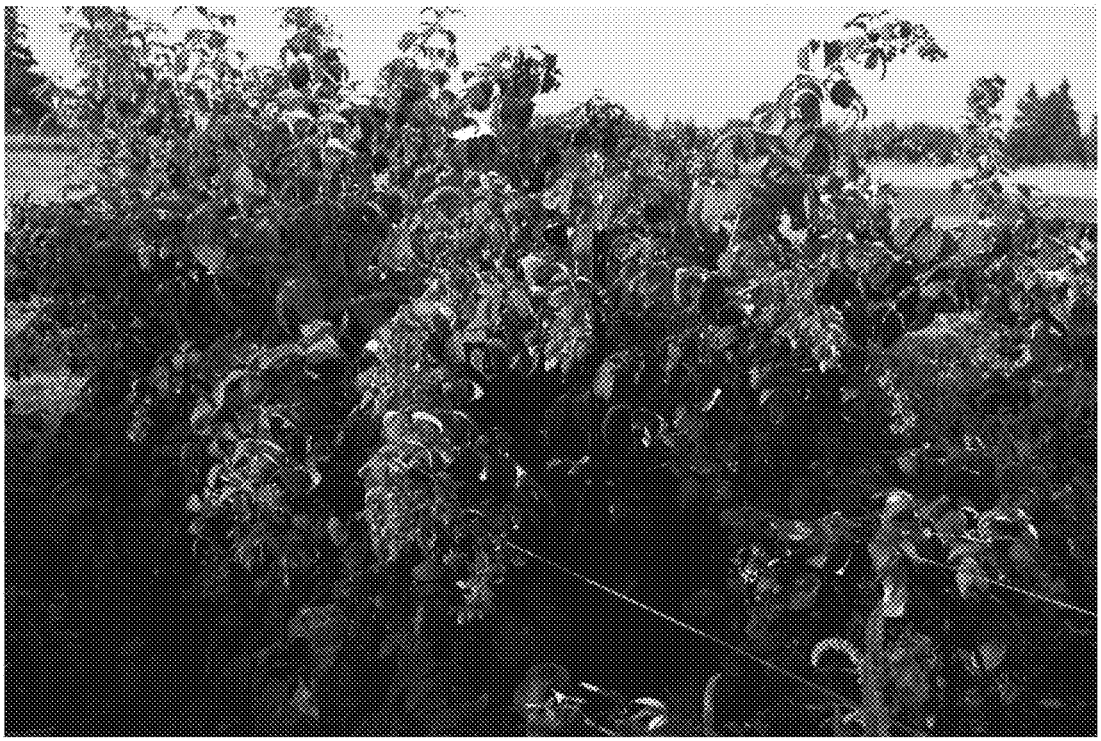
FIG. 5 shows a plot of entire 2-year-old 'Finnberry' plants during ripening season in late August.
Figure 6:
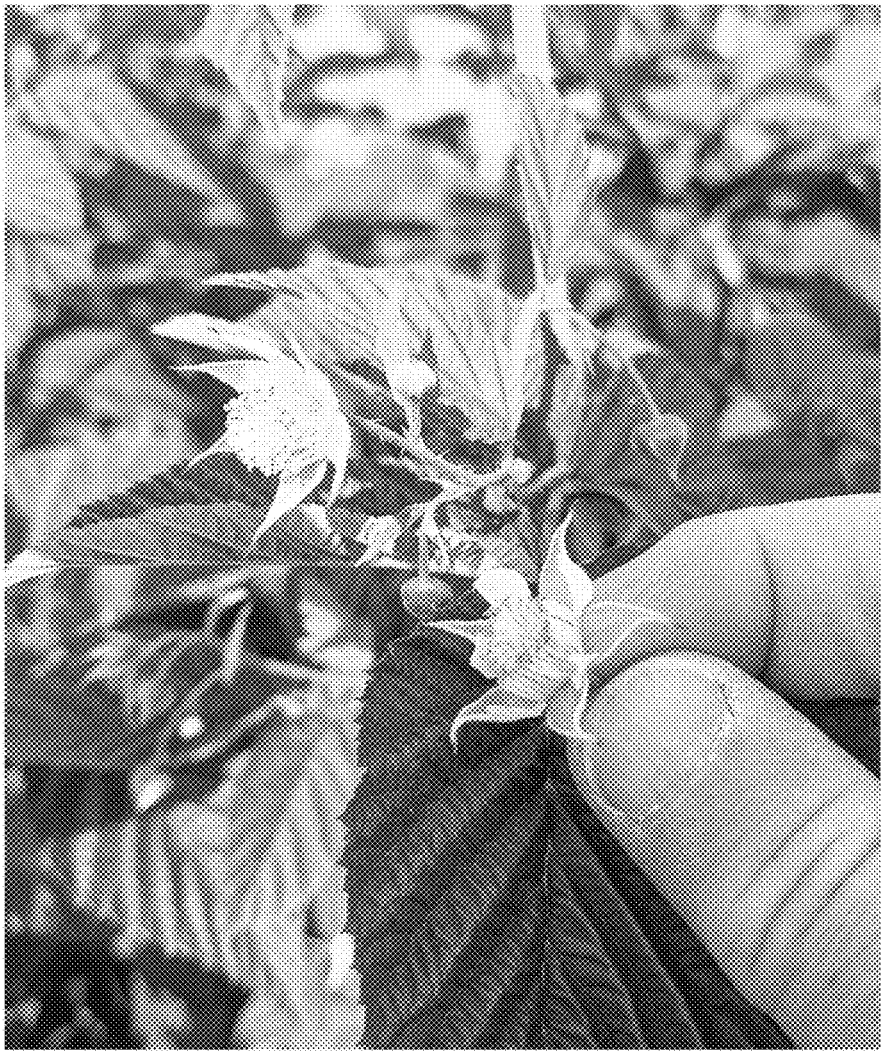
FIG. 6 shows the morphology of a 'Finnberry' flower.

The following description of 'Finnberry' is based on observations taken from 2015 to 2021 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic, and cultural conditions. 'Finnberry' has not been observed under all possible environmental conditions. Color terminology follows The Royal Horticultural Society Colour Chart. London (R.H.S.) ($5^{th}$ edition, 2007).

Table 1 shows plant characteristics of the new cultivar compared with plant characteristics of the red raspberry plant 'Kokanee'. Characteristics include plant size, plant height at first fruit (cm), plant diameter/density/vigor, and number of canes per hill.

TABLE 1

| Characteristic | Finnberry | Kokanee |
|---|---|---|
| Plant size | Large | Large |
| Plant height at first fruit (cm) | 121.0 | 119.2 |
| Plant diameter/density/vigor | Thick/mid/high | Slender/mid-high/high |
| Number of canes per hill | 40.2 | 100.1 |

Table 2 shows primocane characteristics of the new cultivar compared with primocane characteristics of the red raspberry plant 'Kokanee'. Characteristics include new cane habit, timing of young shoots emergence from soil, number of young shoots, very young shoots intensity of anthocyanin coloration, diameter at 1.2 m from base, cane cross-section, length at time of fruit formation, number of nodes, internode length—node 2 to 3 from base, internode length—midpoint, internode length—node 5 to 6 from terminus, cane color, pubescence on canes, percent of cane length flowering as primocane, primocane strength: full-grown after picking, and glaucosity of primocane full-grown after picking.

TABLE 2

| Characteristic | Finnberry | Kokanee |
|---|---|---|
| New cane habit | Erect | Erect |
| Timing of young shoots emergence from soil | Mid-April | Mid-April |
| Number of young shoots | 40 | Many |
| Very young shoots intensity of anthocyanin coloration | Weak/Medium | Absent |
| Diameter at 1.2 m from base (cm) | 0.81 | 0.79 |
| Cane cross-section | Rounded | Rounded |
| Length at time of fruit formation (m) | 1.86 | 1.94 |
| Number of nodes | 32.17 | 33.17 |
| Internode length - node 2 to 3 from base (cm) | 8.13 | 3.47 |
| Internode length - midpoint | 5.88 | 7.77 |
| Internode length - node 5 to 6 from terminus | 3.69 | 7.28 |
| Cane color | RHS 59A | RHS N144D, some blush of 183D and glaucosity of N155A |
| Pubescence on canes | Absent | Absent |
| Percent of cane length flowering as primocane (%) | 21.83 | 36.20 |
| Primocane strength: full-grown after picking | Medium/Strong | Strong |
| Glaucosity of primocane full-grown after picking | Weak | Weak |

Table 3 shows prickle characteristics of the new cultivar compared with prickle characteristics of the red raspberry plant 'Kokanee'. Prickly characteristics include presence of prickles on young shoots, prickle size, prickle length, prickle density, prickle texture, attitude of spine tips, and prickle color.

TABLE 3

| Characteristic | Finnberry | Kokanee |
|---|---|---|
| Prickles on young shoots | Present | Present |
| Prickle size | Medium/Large | Medium |
| [a]Prickle length (cm) | 0.26 | 0.16 |
| [b]Prickle density | Medium, ~250 | Medium, 352 |
| Prickle texture | Stiff | Soft, stout |
| Attitude of spine tips | Horizontal | Horizontal |
| Prickle color | RHS 164A | RHS N144D |

[a]Length of prickles 1 m from ground at end of growing season

[b]Number of prickles on 10 cm section of mature primocane taken at midpoint of cane (dense/medium/sparse/absent)

Table 4 shows primocane leaf characteristics of the new cultivar compared with primocane leaf characteristics of the red raspberry plant 'Kokanee'. Primocane leaf characteristics include: time of budbreak, petiole length (range), petiole length, petiole diameter, petiole color—upper surface, petiole color—lower surface, prickle distribution on petioles, rachis length, rachis color, stipule length, stipule orientation, leaf arrangement, number of leaves per node, entire leaf length, entire leaf width, number of leaflets per leaf, terminal leaflet length, terminal leaflet width, terminal leaflet shape, terminal leaflet tip/apex, terminal leaflet base, terminal leaflet cross section—plane, terminal leaflet shape of teeth, terminal leaflet margin, terminal leaflet petiolule length, terminal leaflet margin, terminal leaflet petiolule length, terminal leaflet petiolule width, distal lateral leaflet length, distal lateral leaflet width, distal lateral leaflet petiolule length, basal lateral leaflet length, basal lateral leaflet width, basal lateral leaflet petiolule length, leaflet color—upper surface, leaflet color—lower surface, and glossiness. In addition to the information in the table, rugosity of the leaf for 'Finnberry' is strong.

TABLE 4

| Characteristic | Finnberry | Kokanee |
|---|---|---|
| Petiole length (range) (cm) | 5.7-7.9 | 2.92-3.86 |
| Petiole length (cm) | 6.92 | 3.37 |
| Petiole diameter (cm) | 0.28 | 0.19 |
| Petiole color - upper surface | RHS 178B | RHS 144C, blush of 183D |
| Petiole color - lower surface | RHS 144C | RHS 144D |
| Prickle distribution on petioles | Sparse/Medium | Sparse |
| Rachis length (cm) | 1.31 | 1.42 |
| Rachis diameter (cm) | 0.20 | 0.17 |
| Rachis color | RHS 178B over 144C | RHS 144C |
| Stipule length (cm) | 0.81 | 0.65 |
| Stipule width (cm) | 0.46 | 0.37 |
| Stipule orientation | Erect | Erect |
| Leaf arrangement | Compound, alternate | Compound, alternate |
| Number of leaves per node | One | One |
| Entire leaf length (cm) | 23.10 | 23.15 |
| Entire leaf width (cm) | 24.73 | 22.82 |
| Number of leaflets per leaf | Usually five | Usually three; ranges one to five |
| Terminal leaflet length (cm) | 10.77 | 13.17 |
| Terminal leaflet width (cm) | 6.57 | 7.73 |
| Terminal leaflet shape | Ovate | Ovate |
| Terminal leaflet tip/apex | Broadly acuminate | Broadly acuminate |
| Terminal leaflet base | Rounded | Ovate |
| Terminal leaflet cross section - plane | Convex | Convex |
| Terminal leaflet shape of teeth | Broadly acuminate | Acute |
| Terminal leaflet margin | Doubly serrate | Serrate |
| Terminal leaflet petiolule length (cm) | 1.86 | 1.64 |
| Terminal leaflet petiolule width (cm) | 0.17 | 0.19 |
| Distal lateral leaflet length (cm) | 8.75 | 9.82 |
| Distal lateral leaflet width (cm) | 4.48 | 4.77 |
| Distal lateral leaflet petiolule length (cm) | 1.21 | - |
| Basal lateral leaflet length (cm) | 10.98 | 11.78 |
| Basal lateral leaflet width (cm) | 6.52 | 7.23 |
| Basal lateral leaflet petiolule length (cm) | 7.75 | - |
| Leaflet color - upper surface | RHS 146A | RHS 137A |
| Leaflet color - lower surface | RHS 198B | RHS 191B |
| Glossiness | Medium | Matte |

Table 5 shows flower characteristics of the new cultivar compared with flower characteristics of the red raspberry plant 'Kokanee'. Flower characteristics include timing of primocane flower bud burst, bud shape—top view, bud shape—side view, bud length, bud diameter, bud color, flower diameter—sepal, flower diameter—petal, diameter of calyx relative to corolla, flower depth (base to top of stigmas), number of nodes/lateral (all nodes are flowering nodes), number of nodes/lateral with >1 flower, number of buds, flowers, fruit per lateral, number of buds, flowers, fruits per node of lateral, petal number, petal length, petal width, petal shape, petal apex, petal base, petal margin, color petals, sepal number, sepal length, sepal width, sepal shape, sepal apex, sepal margin, color sepals—inner surface, color sepals—outer surface, pedicel length, pedicel diameter, pedicel texture, color pedicels, stamen number, filament color, anther length, anther width, anther color—fresh, anther color—dry, pollen color, amount of pollen produced, pistil number, stigma color, stigma shape, style length, style color, and ovary color, as well as measurements related to flowering laterals including peduncle length, peduncle diameter, peduncle texture, and peduncle color.

TABLE 5

| Characteristic | Finnberry | Kokanee |
|---|---|---|
| Timing of primocane flower bud burst | Late June-Mid-July | Late June-Mid-July |
| Bud shape - top view | Pentagonal | Pentagonal to rounded and undulate |
| Bud shape - side view | Deltoid | Deltoid |
| Bud length (cm) | 0.101 | 0.085 |
| Bud diameter (cm) | 0.077 | 0.068 |
| Bud color | RHS 144A | RHS 144B |
| Flower diameter - sepal (cm) | 2.24 | 2.00 |
| Flower diameter - petal (cm) | 2.15 | 1.35 |
| Diameter of calyx relative to corolla | 1.00 | 0.15 |
| Flower depth (base to top of stigmas) | 0.74 | 0.71 |
| Number of nodes/lateral (all nodes are flowering nodes) | 9.00 | 3.67 |
| Number of nodes/lateral with >1 flower | 8.67 | 2.33 |
| Number of buds, flowers, fruit/lateral | 5.67 | 8.67 |
| Number of buds, flowers, fruit/node | 1.67 | 3.83 |
| Petal number | 5.00 | 5.83 |
| Petal length (mm) | 7.30 | 6.89 |
| Petal width (mm) | 3.20 | 3.64 |
| Petal shape | Oblanceolate | Oblanceolate |
| Petal apex | Rounded | Rounded and undulate |
| Petal base | Cuneate | Cuneate |
| Petal margin | Entire | Entire |
| Color petals | RHS NN155B | RHS NN155B |
| Sepal number | 5.00 | 5.83 |
| Sepal length (mm) | 8.80 | 9.31 |
| Sepal width (mm) | 4.65 | 4.69 |
| Sepal shape | Deltoid | Ovoid |
| Sepal apex | Narrowly acuminate | Cuspidate |
| Sepal margin | Entire | Entire |
| Color sepals - inner surface | RHS 145B | RHS 145B |
| Color sepals - outer surface | RHS 144B | RHS 144B base, RHS 144D edges |
| Pedicel length (mm) | 20.22 | 23.29 |
| Pedicel diameter (mm) | 1.05 | 0.93 |
| Pedicel texture | Prickly, echinate | Sparsely prickly |
| Color pedicels | RHS 144B | RHS 144B |
| Stamen number | 111.67 | 94.00 |
| Filament color | RHS NN155C | RHS 196C |
| Anther length (mm) | 0.58 | 0.62 |
| Anther width (mm) | 0.32 | 0.41 |
| Anther color - fresh | RHS NN155A | RHS 157D |
| Anther color - dry | RHS 177B | RHS 158C |
| Pollen color | RHS 156C | RHS NN155D |
| Amount of pollen produce | Abundant | Abundant |
| Pistil number | 95.83 | 92.00 |
| Stigma color | RHS 155C | RHS 155C |
| Stigma shape | Oval | Frayed, ragged |
| Style length (mm) | 2.83 | 3.24 |
| Style color | RHS 157D | RHS 157C |
| Ovary color | RHS 145B | RHS 144C |
| Peduncle length (mm) | 100.62 | 18.97 |
| Peduncle diameter (mm) | 2.10 | 1.33 |
| Peduncle texture | Smooth | Sparsely prickly |
| Peduncle color | RHS 59A | RHS 144B |

Table 6 shows fruit characteristics of the new cultivar compared with fruit characteristics of the red raspberry plant 'Kokanee'. Fruit characteristics include length, width, length/width ratio, receptacle length, receptacle diameter, drupelet length, drupelet width, number of drupelets per fruit, fruit weight, drupelet weight, individual seed weight, total seed weight per fruit, seed length, seed width, seed color, fruit glossiness, separation from receptacle, drupelet cohesion, firmness, flavor, fruit color, fruit color—immature, fruit color—maturing, fruit color—mature, titratable acidity, soluble solids, pH, harvest season, length of season, yield, and productivity. Fruit chemistry measurements were collected during the 2021 field season. In addition to the information in the table, the shape of 'Finnberry' fruit is blunt-conical/rounded.

TABLE 6

| Characteristic | Finnberry | Kokanee |
|---|---|---|
| Length (mm) | 23.45 | 22.50 |
| Width (mm) | 20.72 | 19.33 |
| Length/width ratio | 1.13 | 1.16 |
| Receptacle length (mm) | 17.08 | 12.19 |
| Receptacle diameter (mm) | 7.42 | 5.85 |
| Drupelet length (mm) | 4.73 | 3.30 |
| Drupelet width (mm) | 3.47 | 3.20 |
| Number of drupelets per fruit | 116 | 132 |
| Weight (g) | 3.90 | 3.35 |
| Drupelet weight (mg) | 34.60 | 25.98 |
| Individual seed weight (mg) | 1.52 | 1.27 |
| Total seed weight per fruit (mg) | 180.00 | 165.65 |
| Seed length (mm) | 3.27 | 2.30 |
| Seed width (mm) | 1.40 | 1.33 |
| Seed color (dry) | RHS 165D | RHS 156A |
| Glossiness | Low/Medium | Medium |
| Separation from receptacle | Very easy | Very easy |
| Drupelet cohesion | Coherent | Coherent |
| Firmness | Firm | Firm |
| Flavor | Very good | Very good |
| Fruit color | Bright | Bright |
| Fruit color - immature | RHS 163B to RHS 163C | RHS 164C |
| Fruit color - maturing | RHS 34D | RHS 47A |
| Fruit color - mature | RHS 185A | RHS 53A |
| Titratable acidity (% as citric acid) | 20.00 | 13.70 |
| Soluble solids (%; in Brix) | 14.27 | 13.96 |
| pH | 3.17 | 3.39 |
| Harvest season | 18 Aug-30 Sept | 9 Aug-18 Sept |
| Length of season | Medium | Medium |
| Yield (kg/plant) | 3.49 | 2.30 |
| Productivity | High | Medium-high |

No particular resistance or susceptibility to pests or disease have been observed in 'Finnberry' to date. 'Finnberry' has been shown to grow in plant hardiness zone 8a-8b and has not been thoroughly evaluated outside of that zone.

COMPARISON WITH PARENTAL AND COMMERCIAL VARIETIES

'Finnberry' differs from the female parent red raspberry plant 'Caroline' in that it produces significantly higher yields of fruit with superior fresh market quality including firmness and drupelet coherence. The 'Finnberry' fruit are larger than 'Caroline' and show easier separation for ease of picking. In trials in Aurora, Oreg., 'Caroline' was observed to produce fruit that were flavorful but more susceptible to crumbling, and weaker plants that showed some susceptibility to root rot (a symptom typically associated with the disease-causing pathogen *Phytophthora rubi*).

'Finnberry' differs from the male parent red raspberry plant ORUS 4099-1 in that it produces greater yields of fruit with improved quality for the fresh market. The fruit of ORUS 4099-1 were noted for becoming a bit dark and soft after picking, while 'Finnberry' fruit were lighter colored and less glossy but retained better firmness and quality after picking.

'Finnberry' differs from the primocane-fruiting red raspberry varieties 'Kokanee', 'Heritage', 'Vintage', and 'Polka' in that it has been consistently as high or higher yielding in trials in Aurora, Oreg., and is later-ripening than each variety except for 'Heritage', which ripens at a similar time in the mid-to-late season. 'Finnberry' produces bright colored fruit that retained a more favorable appearance and quality than 'Kokanee' and 'Polka' after 14 days in refrigerated storage in plastic clamshell packaging at 4° C. The 'Finnberry' fruit are larger than 'Kokanee', 'Vintage', and 'Heritage' and similar in size to 'Polka'. The fruit flavor is described as tangy and slightly acidic, with a mild sweetness and good aroma, and ranked higher than 'Kokanee', 'Heritage', 'Vintage', and 'Polka' in a 2019 stakeholder survey of fruit samples conducted by Oregon State University's department of Food Science. The fruit appear to have higher firmness and lower defects from heat and UV compared to 'Kokanee', 'Heritage' and 'Vintage'.

We claim:

1. A new and distinct cultivar of primocane-fruiting red raspberry plant named 'Finnberry', substantially as illustrated and described, characterized by its high yields of medium-to-large sized berries with excellent fresh market eating quality, firmness, flavor, and low fruit defects, and the ability to be picked at early/pink stages with good flavor and firmness.

* * * * *